(12) United States Patent
Neuenhofer et al.

(10) Patent No.: US 7,252,961 B2
(45) Date of Patent: Aug. 7, 2007

(54) COMPETITIVE IMMUNOASSAY USING COMPLEXED ANALYTE DERIVATIVES

(75) Inventors: Stephan Neuenhofer, Marburg (DE); Heinz-Jürgen Skrzipczyk, Zeppelinheim (DE); Peter Molz, Mainz (DE); Reinhard Käsmarker, Marburg (DE)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 08/895,862

(22) Filed: Jul. 17, 1997

(65) Prior Publication Data

US 2003/0073126 A1 Apr. 17, 2003

Related U.S. Application Data

(63) Continuation of application No. 08/598,263, filed on Feb. 7, 1996, now abandoned.

(30) Foreign Application Priority Data

Feb. 9, 1995 (DE) ................................ 195 04 198

(51) Int. Cl.
*G01N 33/533* (2006.01)

(52) U.S. Cl. .................... 435/7.93; 435/7.1; 435/7.92; 435/7.95; 436/500; 436/514; 436/518; 436/501; 436/507; 436/538; 436/824; 436/825; 424/1.49

(58) Field of Classification Search ....... 435/7.92–7.95, 435/973, 7.9, 7.1; 436/500, 501, 528, 518, 436/507, 538, 824, 825; 424/1.49
See application file for complete search history.

(56) References Cited

U.S. PATENT DOCUMENTS

| | | | | |
|---|---|---|---|---|
| 4,745,072 A | * | 5/1988 | Ekins et al. | 436/500 |
| 4,839,299 A | * | 6/1989 | Charlton et al. | 436/500 |
| 5,143,852 A | * | 9/1992 | Valkirs et al. | 436/501 |
| 5,164,299 A | * | 11/1992 | Lambert | 435/7.92 |
| 5,312,763 A | * | 5/1994 | Baumgarten et al. | 436/518 |
| 5,332,679 A | * | 7/1994 | Simons et al. | 436/518 |
| 5,527,686 A | * | 6/1996 | Fitzpatrick et al. | 435/7.9 |
| 5,589,344 A | * | 12/1996 | Contestable et al. | 435/7.9 |

FOREIGN PATENT DOCUMENTS

| | | |
|---|---|---|
| EP | 0 103 605 B1 | 3/1984 |
| EP | 0 026 103 B1 | 4/1985 |
| EP | 0 254 929 B1 | 2/1988 |
| EP | 0 303 284 A1 | 2/1989 |
| EP | 0 303 284 B1 | 2/1989 |
| EP | 0 182 385 B1 | 5/1989 |
| EP | 0 324 540 B1 | 7/1989 |
| WO | WO 89/06363 | 7/1989 |

OTHER PUBLICATIONS

Harlow et al., Antibodies: A Laboratory Manual. Cold Spring Harbor Laboratory 1988, pp. iii-ix (Table of Contents).

* cited by examiner

*Primary Examiner*—Bao-Thuy L. Nguyen
(74) *Attorney, Agent, or Firm*—Finnegan, Henderson, Farabow, Garrett and Dunner, L.L.P.

(57) ABSTRACT

The invention relates to a method for the detection of an analyte in a competitive immunoassay in the presence of an analyte derivative and first and second receptor molecules, and to a kit for carrying out this detection method.

22 Claims, 2 Drawing Sheets

COMPETITIVE IMMUNOASSAY USING COMPLEXED ANALYTE DERIVATIVES

This application is a continuation, of application Ser. No. 08/598,263, filed Feb. 7, 1996, now abandoned.

BACKGROUND OF THE INVENTION

The invention relates to a method for the detection of an analyte in a competitive immunoassay in the presence of an analyte derivative, and to a kit for carrying out this detection method.

Immunological detection methods have gained great importance in in vitro diagnosis. The reason for this is that they are highly specific and extremely sensitive. Moreover, these assays are distinguished by simple handling. The detection methods are based on the immunological interaction between the analyte to be detected and its binding partner or partners.

In the case of sandwich assays, the analyte is bound like a sandwich by two different antibodies. One of the two antibodies carries a label (marker), whereby its concentration can be determined. In the case of small analytes, the sandwich method is excluded, as for steric reasons two different antibodies can not simultaneously bind to the analyte. Here, as a rule, competitive assays are used. In these, the analyte and a synthetic derivative of the analyte compete for the binding sites of the antibody. As a rule, either the analyte derivative (classic competitive method) or the antibody is labeled.

Often, the antibody is bound in the classic competitive method to a solid phase, while in the method using labeled antibody the analyte derivative is immobilized (solid phase antigen techniques, e.g. SPALT=solid phase antigen luminescence technique).

In the competitive assay method the methods using labeled antibodies have gained particular importance in the determination of the freely available portion of an analyte. "Freely available" here means that these analytes are not bound as ligands by their natural receptors, which can occur, for example in the serum. Methods of this type have gained importance, for example, in the determination of free triiodothyronine (FT3) and free thyroxine (FT4). In order to be able to determine the proportion of analyte independently of the concentration of binding proteins occurring in the sample (for example serum proteins), the analyte derivative must change its properties on binding to, solid phases in such a way that it can still interact with the antibody, but not—or only insignificantly—with the binding protein. A method of this type was described as a 1-step assay, for example, in EP-A-0 103 605.

This method using labeled antibodies, in particular, has the advantage of easy tracer preparation, as the labeling of an antibody is not a problem in most cases. It is therefore still to be preferred to the classical competitive method if an analyte tracer is available which shows the abovementioned, desired binding behavior (EP-A-0 026 103).

When carrying out the abovementioned method, the choice of an analyte derivative having suitable affinity for the antibody often causes problems. These result from the fact that the affinity of the. analyte derivative for the antibody for a meaningful assay result must be in a certain ratio to the affinity of the analyte for the antibody (cf. EP-A-0 254 929, EP-A-0 324 540, EP-A-0 303 284). If, for example, the affinity of the analyte derivative for the antibody is too high, the reaction equilibrium in the assay mixture will shift too much in the direction of the antibody-analyte derivative complex, which leads to a reduction in the meaningfulness of the assay. In order to remedy this disadvantage, a preincubation of the analyte with the antibody can be carried out (cf. EP-A-0 182 385). If, on the other hand, the affinity of the analyte derivative is too low, a preincubation of analyte derivative and antibody first can be of use. A disadvantage in both cases, however, is the necessity of having to carry out the assay in two steps. A possibility of circumventing this disadvantage consists in chemically modifying the analyte derivative in order to produce a suitable affinity for the antibody. However, a method of this type is also laborious and, with small analyte derivatives, often associated with difficulties or not possible to carry out at all.

SUMMARY OF THE INVENTION

The present invention is thus based on the object of providing a method for the detection of an analyte in competitive immunoassays which overcomes the disadvantages described above. This object is achieved by the embodiments provided in the claims.

The invention thus relates to a method for the detection of an analyte in a competitive immunoassay which comprises carrying out the following steps:

(a) incubation of an analyte derivative with a sample containing the analyte and a first receptor molecule specific for analyte and analyte derivative, the incubation mixture also containing a second receptor molecule which specifically binds the analyte derivative or the analyte derivative and the analyte;

(b) separation of the first receptor molecule not bound to the analyte derivative; or (b') separation of the analyte derivative not bound to the first receptor molecule; and (c) detection of the first receptor molecule bound to the analyte derivative or of the analyte derivative bound to the first receptor molecule.

The abovementioned step (b) is carried out if the analyte derivative is bound to a solid phase. On the other hand, step (b') is carried out if the first receptor molecule is bound to a solid phase.

The term "analyte" within the meaning of this invention signifies any molecule which occurs in a sample, preferably a biological sample, and can be bound by a receptor molecule.

The term "analyte derivative" signifies a substance which cross reacts with the receptor molecule directed against the analyte.

The term "receptor molecule" relates to any molecule which has a specific binding site for another molecule, e.g. an analyte. Examples of receptor molecules are hormone receptors or antibodies. The receptor molecules can be of natural, recombinant, synthetic or semisynthetic origin.

The second receptor molecule specific for the analyte derivative can, but need not cross react with the analyte. It is customarily different from the first receptor molecule. Moreover, it can carry a label which, however, is different from the label of the first receptor molecule if the first receptor molecule is labeled.

Using the method according to the invention, analytes in a sample can easily be detected qualitatively, and quantitatively. This result is achieved in that the analyte derivative is masked by the second receptor molecule specific therefor and the affinity of the first receptor molecule for the analyte derivative is thus reduced. The consequence of this is that the reaction equilibrium in the incubation mixture is shifted in the direction analyte-analyte-specific first receptor molecule. By means of the use of different analyte derivative-specific molecules, the reactivity of the analyte derivative or of the complex of analyte derivative and analyte derivative-specific second receptor molecule can be varied in a simple manner relative to the analyte-specific first receptor molecule. A further degree of freedom for optimizing the assay is thereby available.

It is known to the person skilled in the art which materials he can use as solid phases and which conditions he employs for carrying out the method according to the invention. Materials and conditions of this type are preferably of the customary type, such as described, for example, in Harlow and Lane, "Antibodies, A Laboratory Manual", CSH-Press, Cold Spring Harbor, 1988. Moreover, the person skilled in the art knows that washing steps using suitable buffers are to be carried out between the individual steps mentioned above. The Harlow and Lane document, loc. cit., for example, also serves here as a guide. It is further known to the person skilled in the art how he chooses the time and temperature for the individual steps mentioned in the method according to the invention. Preferably, the temperature is between room temperature (customarily about 22° C.) and 37° C. A particularly preferred temperature for the incubation is 37° C. The detection of the first receptor molecule bound to the analyte derivative or of the analyte derivative bound to the first receptor molecule also takes place according to customary methods, for example by measurement of a signal which is emitted by the labeled analyte derivative or the labeled first receptor molecule. If neither analyte derivative nor first receptor molecule are labeled, the detection can be carried out using a second labeled antibody or antibody fragment which is specific, for example, for the first receptor molecule.

DESCRIPTION OF THE INVENTION

Figure 1:
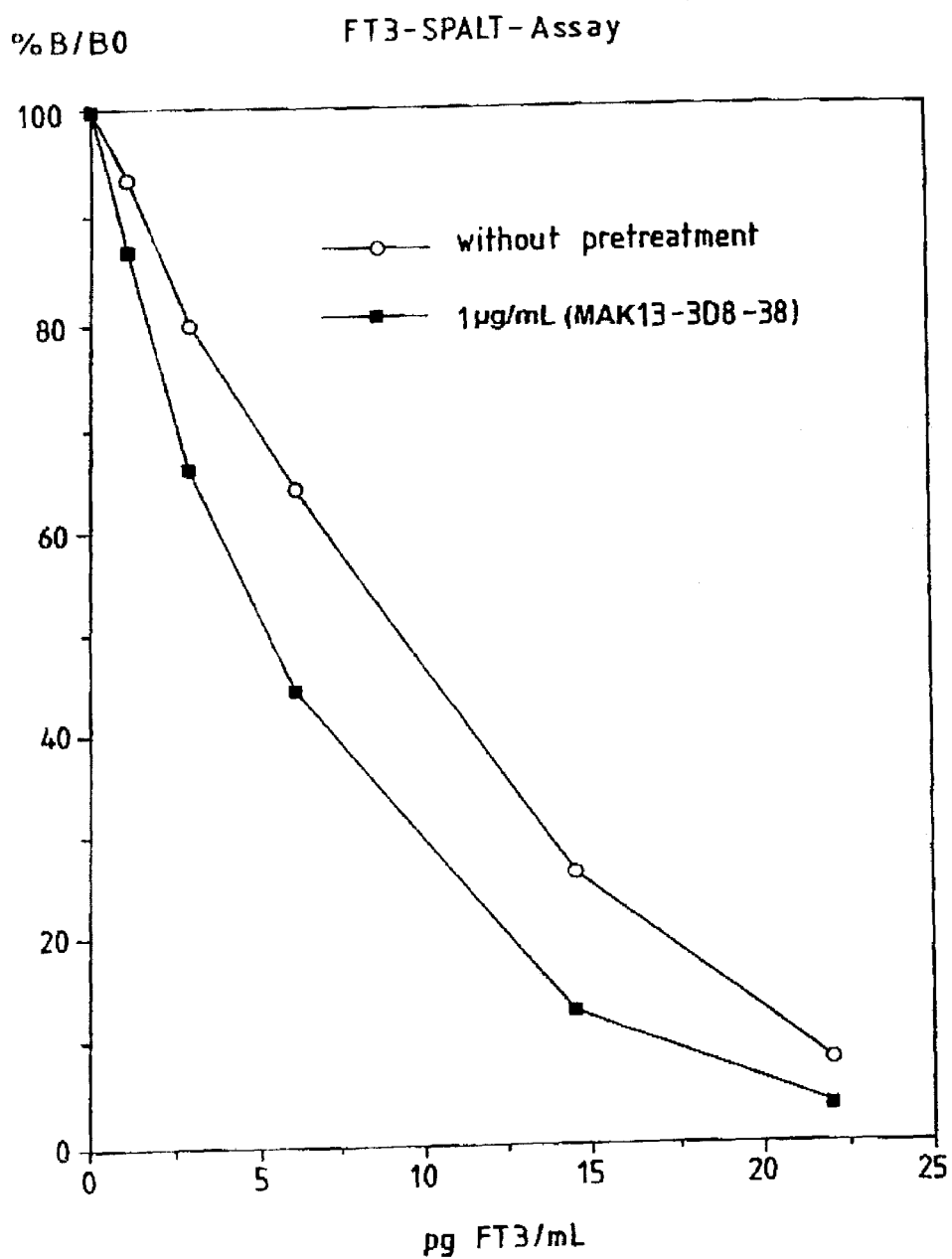
FIG. 1 shows FT3 luminescence immunoassay by the SPALT method. The solid phase used is protein T3 conjugate (=analyte derivative)-coated tubes (upper curve). By masking the analyte derivative with an anti-estradiol T3 antibody, a standard curve having higher signal dynamics is obtained (lower curve).

In a preferred embodiment of the method according to the invention, the analyte derivative is incubated with the second receptor molecule before incubation with the sample and the first receptor molecule.

This first incubation step has the consequence that the analyte derivative is introduced into the incubation mixture already masked. A further advantage lies in the fact that a smaller amount of analyte-specific second receptor molecule is necessary in order to mask the analyte derivative completely or almost completely. If both receptor molecules are incubated with the analyte derivative simultaneously, these compete for the available binding sites on the analyte derivative. This has the consequence that a larger amount of second receptor molecule has to be employed for carrying out the assay.

In a further preferred embodiment of the method according to the invention, the first receptor molecule is labeled, In this embodiment, the labeling of the first receptor molecule serves for the detection of the analyte.

In a further preferred embodiment of the method according to the invention, the analyte derivative is labeled.

The labeling of the receptor molecule or of the analyte derivative can be of a variety of types. Particularly preferred according to the invention are a radioactive, chemiluminescent, bioluminescent, fluorescent, phosphorescent or electroluminescent label, an enzyme, biotin or a group capable of absorption.

A further preferred embodiment of the method according to the invention comprises binding the analyte derivative to a solid phase. In this embodiment, the analyte derivative is preferably unlabeled. Examples of solid phases which can be used in the method according to the invention are microtiter plates, preferably made of polystyrene, polymer beads, tubes or membranes.

In a further preferred embodiment of the method according to the invention, the analyte derivative is incubated with the second receptor molecule after binding to the solid phase. This embodiment has the particular advantage that solid phases which are first coated with the analyte derivative, e.g. microtiter plates, can be prepared which can also be stored for a longer term under customary conditions before use in the analytical method according to the invention.

A further preferred embodiment of the method according to the invention comprises binding the first receptor molecule to a solid phase.

In a further preferred embodiment of the method according to the invention, the analyte derivative is incubated with the second receptor molecule after binding the first receptor molecule to the solid phase.

This embodiment also has the particular advantage that the solid phases can be stored under suitable conditions for a longer term after binding the first receptor molecule before use in the analytical method according to the invention.

An embodiment is further preferred in which the first and the second receptor molecule are identical with the exception of the label.

An embodiment is further preferred in which the first and the second receptor molecule are different. Customarily, two different antibodies will be used in the assay according to the invention.

In a further preferred embodiment, the first and/or the second receptor molecule is/are an antibody or an antibody fragment.

The antibody used here can be a polyclonal, a monoclonal, a chimeric or a synthetically produced antibody. The preparation of antibodies of this type is known in the prior art and described, for example, in Harlow and Lane, loc. cit. Antibody fragments are likewise known in the prior art. Within the meaning of the invention, it is at most necessary that they can bind the analyte derivative or the analyte specifically and, if they are used as the first receptor molecule, can be provided with a suitable label. Examples of antibody fragments are Fv, Fab or $F(ab)_2$ fragments.

In a further preferred embodiment of the method according to the invention, the analyte is a ligand. "Ligand" is understood according to the invention as meaning any molecule for which a naturally occurring receptor binding this molecule exists. Preferably, the ligand is a naturally occurring molecule and, particularly preferably, this molecule occurs in body fluids, for example in serum.

In a particularly preferred embodiment of the method according to the invention, the ligand is thyroxine, triiodothyronine or a steroid, for example estradiol.

In a further preferred embodiment of the method according to the invention, a preincubation of the analyte with the first receptor molecule is carried out before step (a). An achievement of this embodiment is that a substantial amount of free analyte, in particular ligand, is bound, which in turn has favorable effects on the quantitative detection of this ligand in the assay system according to the invention.

The preincubation step is preferably carried out for 5 to 30 minutes.

The invention further relates to a kit which contains at least (a) an analyte derivative; and/or (b) a labeled analyte derivative; and (c) a first receptor molecule specific for an analyte and the analyte derivative; and/or (d) a first labeled receptor molecule specific for an analyte and the analyte derivative; and (e) a second receptor molecule which specifically binds the analyte derivative or the analyte derivative and the analyte.

The person skilled in the art can supplement the kit according to the invention by further customary components, e.g. suitable buffers.

The invention finally relates to the use of the kit according to the invention for carrying out the method according to the invention.

The following examples illustrate the invention.

EXAMPLE 1

To BERILUX® T3 (Behringwerke AG, Marburg)—coated tubes (tubes which are coated with a protein-T3 conjugate) is added 0.5 ml of an anti-T3 antibody solution (1 µg of unlabeled BERILUX® T3 tracer antibody/ml of incubation buffer). After incubation at 37° C. for 2 hours, the solution is removed and the tubes are washed once with 1 ml of wash buffer. The tubes pretreated in this way are employed as a solid phase in an FT3 assay using labeled anti-T3 antibody as a tracer. The signal dynamics obtained are higher than in the case of the untreated tubes (FIG. 1).

Incubation Buffer:

0.1 M phosphate buffer, pH 7.4 containing 1 g of bovine IgG, 8 g of NaCl and 1 g of sodium azide per liter.

Tracer:

30 ng of BERILUX® T3 tracer antibody per ml of 0.1 M phosphate buffer, pH 7.4 containing 1 g of bovine IgG, 8 g of NaCl and 1 g of sodium azide per liter (BERILUX® T3-Tracerantibodies=MAK 13-3D8-38; Manufacturer: Immunogen International Ltd., United Kingdom).

Wash Buffer:

0.1 M phosphate buffer, pH 7.4 containing 8 g of NaCl per liter.

Assay Conditions:

100 ml of sample (standard or serum) and 200 µl of tracer are shaken at room temperature for 60 minutes. After washing four times with 1 ml of wash buffer each time, the signal activity is measured in the BERILUX® analysis apparatus.

EXAMPLE 2

Figure 2:
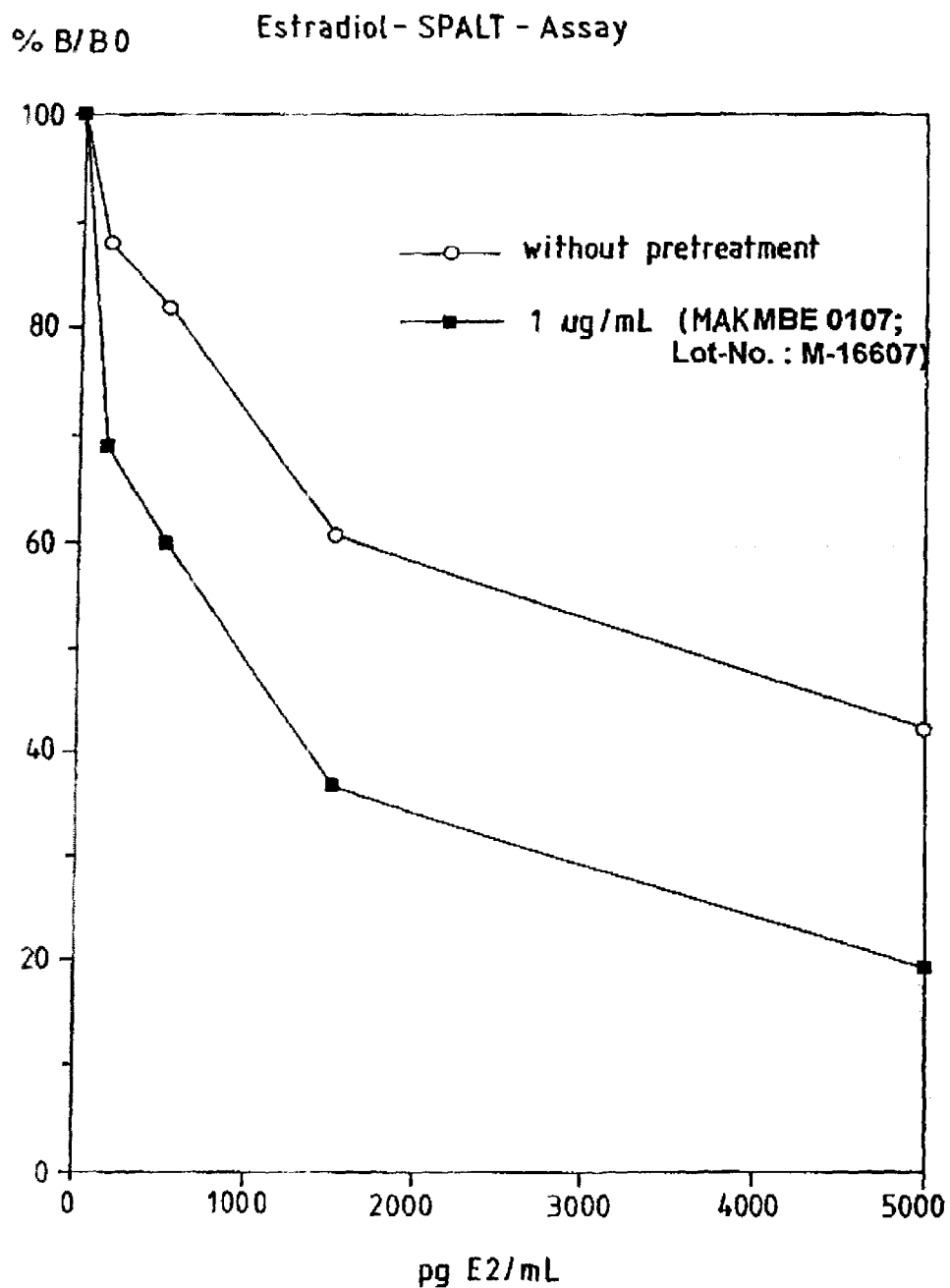
FIG. 2 shows SPALT assay for the determination of estradiol. The solid phase used is protein-estradiol conjugate (=analyte derivative)-coated tubes (upper curve). By masking the analyte derivative with an anti-estradiol antibody, a standard curve having higher signal dynamics is obtained (lower curve).

1 mg of magnetic particles which have been coated with an IgG-estradiol conjugate are brought into contact with 8 ml of a solution which contains 1 µg of anti-estradiol antibody (Medix-Biotech, Cat. No. MBE 0107; Lot-no.M-16607)/ml of incubation buffer. After incubation at 37° C. for one hour, the. magnetic particles are washed and employed as the solid phase in an estradiol SPALT assay. The tracer used is an anti-estradiol antibody (BiosPacific, Clone No. A 54010014 P) labeled with BERILUX® label. The standard curve obtained with the magnetic particles treated in this way has higher signal dynamics than that which is obtained under identical conditions with the solid phase which is not aftertreated (FIG. 2).

Incubation buffer:

0.1 M Tris/HCl buffer, pH 8.0 containing 8.7 g of NaCl, 1 g of bovine IgG, 1 g of TWEEN® 20 and 1 g of sodium azide per liter.

Tracer:

10 ng of anti-estradiol antibody (BiosPacific) per ml of 0.1 M phosphate buffer, pH 6.3 containing 5.9 g of NaCl, 1 g of bovine IgG, 1 g of sodium azide, 15 mg of danazol and 15 mg of hydrocortisone per liter.

Wash buffer:

0.1 M phosphate buffer, pH 7.4 containing 8.0 g of NaCl per liter.

Assay Conditions:

20 µl of magnetic particle suspension (25 µg of coated magnetic particles)+100 µl of sample (standard or serum) and 200 µl of tracer are incubated at 37° C. for 30 minutes. After washing three times with 0.5 ml of wash buffer each time, the signal activity is measured in the BERILUX® analysis apparatus.

The invention claimed is:

1. A method for determining the presence or amount of an analyte in a sample in a competitive immunoassay, which comprises the following steps:

(a) incubating an analyte derivative with the sample, a first receptor molecule which is specific for the analyte and the analyte derivative, and a second receptor molecule which is specific for the analyte derivative and the analyte, wherein the analyte derivative is immobilized on a solid phase;

(b) binding the analyte derivative with the first receptor molecule, wherein the first receptor molecule is labeled with a label, and wherein the second receptor molecule masks the analyte derivative;

(c) separating the first receptor molecule not bound to the analyte derivative; and (d) detecting the first receptor molecule bound to the analyte derivative and determining the presence or amount of the analyte in the sample.

2. The method of claim 1, wherein prior to step (a) the analyte derivative is incubated with the second receptor molecule which is specific for the analyte derivative and the analyte to form a pre-incubated analyte derivative and wherein step (a) comprises incubating the sample, a first receptor molecule which is specific for the analyte and the analyte derivative, and the pre-incubated analyte derivative, wherein the pre-incubated analyte derivative is immobilized on a solid phase.

3. The method of claim 1, wherein the label is selected from the group consisting of a radioactive label, chemiluminescent label, bioluminescent label, fluorescent label, phosphorescent label, electroluminescent label, an enzyme, biotin, and a group capable of absorption.

4. The method of claim 1, wherein step (a) comprises three steps, step a1, step a2, and step a3 and wherein step a1 comprises immobilizing the analyte derivative on a solid phase;

step a2 comprises incubating the immobilized analyte derivative with the second receptor molecule to form a pre-incubated analyte derivative; and step a3 comprises incubating the sample, the first receptor molecule which is specific for the analyte and the analyte derivative, and the pre-incubated analyte derivative.

5. The method of claim 1, wherein the first and the second receptor molecule are identical with the exception of a label.

6. The method of claim 1, wherein the first and the second receptor molecule are different.

7. The method of claim 1, wherein the first or the second receptor molecule, or both, are an antibody or an antibody fragment.

8. The method of claim 1, wherein the analyte is a ligand.

9. The method of claim 1, wherein the ligand is thyroxine, triiodothyronine or a steroid.

10. The method of claim 1, wherein prior to step (a) the sample is incubated with the first receptor molecule.

11. A method for determining the presence or amount of an analyte in a sample in a competitive immunoassay, which comprises the following steps:
   (a) incubating an analyte derivative with the sample, a first receptor molecule which is specific for the analyte and the analyte derivative, and a second receptor molecule which is specific for the analyte derivative and the analyte, wherein the first receptor molecule is immobilized on a solid phase;
   (b) binding the analyte derivative with the first receptor molecule, wherein the analyte derivative is labeled with a label, and wherein the second receptor molecule masks the analyte derivative;
   (c) separating the analyte derivative not bound to the first receptor molecule; and
   (d) detecting the analyte derivative bound to the first receptor molecule and determining the presence or amount of the analyte in the sample.

12. The method of claim 11, wherein prior to step (a) the analyte derivative is incubated with the second receptor molecule which is specific for the analyte derivative and the analyte to form a pre-incubated analyte derivative and wherein step (a) comprises incubating the sample, the first receptor molecule which is specific for the analyte and the analyte derivative, and the pre-incubated analyte derivative, wherein the pre-incubated analyte derivative is immobilized on a solid phase.

13. The method of claim 11, wherein the label is selected from the group consisting of a radioactive label, chemiluminescent label, bioluminescent label, fluorescent label, phosphorescent label, electroluminescent label, an enzyme, biotin, and a group capable of absorption.

14. The method of claim 11, wherein step (a) comprises three steps, step a1, step a2, and step a3 and wherein
   step a1 comprises immobilizing the first receptor molecule on a solid phase;
   step a2 comprises incubating the analyte derivative with the second receptor molecule to form a pre-incubated analyte derivative; and
   step a3 comprises incubating the sample, the immobilized first receptor molecule which is specific for the analyte and the analyte derivative, and the pre-incubated analyte derivative.

15. The method of claim 11, wherein the first and the second receptor molecule are identical with the exception of a label.

16. The method of claim 11, wherein the first and the second receptor molecule are different.

17. The method of claim 11, wherein the first or the second receptor molecule, or both, are an antibody or an antibody fragment.

18. The method of claim 11, wherein the analyte is a ligand.

19. The method of claim 18, wherein the ligand is thyroxine, triiodothyronine or a steroid.

20. The method of claim 12, wherein prior to step (a) the sample is incubated with the first receptor molecule.

21. A kit for performing the method of claim 1, said kit comprising:
   (a) an analyte derivative, a labeled analyte derivative, or both;
   (b) a first receptor molecule specific for an analyte and the analyte derivative, a first labeled receptor molecule specific for an analyte, or the analyte derivative, or both; and
   (c) a second receptor molecule specific for the analyte derivative and the analyte.

22. A kit for performing the method of claim 11, said kit comprising:
   (a) an analyte derivative, a labeled analyte derivative, or both;
   (b) a first receptor molecule specific for an analyte and the analyte derivative, a first labeled receptor molecule specific for an analyte, or the analyte derivative, or both; and
   (c) a second receptor molecule specific for the analyte derivative and the analyte.

* * * * *